United States Patent
Kogure

(10) Patent No.: US 10,362,642 B2
(45) Date of Patent: Jul. 23, 2019

(54) LIGHT EMITTING DEVICE AND LIGHT ILLUMINATING APPARATUS COMPRISING THE LIGHT EMITTING DEVICE

(71) Applicant: HOYA CANDEO OPTRONICS CORPORATION, Toda-shi, Saitama (JP)

(72) Inventor: Yasuo Kogure, Toda (JP)

(73) Assignee: HOYA CANDEO OPTRONICS CORPORATION, Toda-Shi, Saitama (JP)

( * ) Notice: Subject to any disclaimer, the term of this patent is extended or adjusted under 35 U.S.C. 154(b) by 0 days.

(21) Appl. No.: 15/939,242

(22) Filed: Mar. 28, 2018

(65) Prior Publication Data
US 2018/0288840 A1 Oct. 4, 2018

(30) Foreign Application Priority Data
Mar. 29, 2017 (JP) .................. 2017-065277

(51) Int. Cl.

| | |
|---|---|
| H01L 51/52 | (2006.01) |
| H05B 37/02 | (2006.01) |
| H05B 33/08 | (2006.01) |
| A61B 1/06 | (2006.01) |
| F21S 2/00 | (2016.01) |
| H01L 25/075 | (2006.01) |

(Continued)

(52) U.S. Cl.
CPC ....... *H05B 33/0803* (2013.01); *A61B 1/0684* (2013.01); *F21S 2/005* (2013.01); *H01L 25/0753* (2013.01); *H01L 51/5206* (2013.01); *H01L 51/5221* (2013.01); *H05B 37/02* (2013.01); *F21Y 2103/10* (2016.08); *F21Y 2115/10* (2016.08)

(58) Field of Classification Search
None
See application file for complete search history.

(56) References Cited

U.S. PATENT DOCUMENTS

| 2006/0171135 A1 | 8/2006 | Ishizaka et al. |
| 2006/0284199 A1 | 12/2006 | Matheson |

(Continued)

FOREIGN PATENT DOCUMENTS

| JP | 2006-261039 A | 9/2006 |
| JP | 2010-199005 A | 9/2010 |
| KR | 2013-0016845 A | 2/2013 |

*Primary Examiner* — Dedei K Hammond
(74) *Attorney, Agent, or Firm* — Rabin & Berdo, P.C.

(57) ABSTRACT

(Problem)
To provide technology for easily manufacturing a light illuminating apparatus suitable for the performance of a power device
(Problem-solving means)
A light emitting device (M) includes a substrate (410) having an anode pattern (310) and a cathode pattern (320), and at least one light emitting element (330) connected to the anode pattern and the cathode pattern. The substrate has a connecting part (350) at each of two ends of the anode pattern extending in a connection direction with other light emitting device that is different from the light emitting device (M) to connect the light emitting device (M) to other light emitting device, and a connecting part (350) at each of two ends of the cathode pattern extending in the connection direction to connect the light emitting device (M) to other light emitting device.

20 Claims, 20 Drawing Sheets

(51) Int. Cl.
 *F21Y 103/10* (2016.01)
 *F21Y 115/10* (2016.01)

(56) References Cited

U.S. PATENT DOCUMENTS

| | | | |
|---|---|---|---|
| 2011/0133217 A1* | 6/2011 | Hakamata | H01L 25/0753 257/88 |
| 2013/0087722 A1 | 4/2013 | Brown | |
| 2015/0276198 A1* | 10/2015 | Hata | H01L 25/0753 362/382 |
| 2017/0067627 A1 | 3/2017 | Liu et al. | |

* cited by examiner

LIGHT EMITTING DEVICE AND LIGHT ILLUMINATING APPARATUS COMPRISING THE LIGHT EMITTING DEVICE

TECHNICAL FIELD

The present disclosure relates to a light emitting device, and more particularly, to a light emitting device with structure for connection with other light emitting device.

BACKGROUND ART

Recently, light emitting devices are used for various purposes. For example, light emitting devices are used for liquid crystal display backlights, lighting for plant growth and medical lighting such as endoscopy. There are various types of light emitting devices including incandescent light bulb, fluorescent light and Light Emitting Diode (LED) lighting. Additionally, light emitting devices irradiate visible light as well as ultraviolet (UV) light. For example, Flat Panel Display (FPD) such as a liquid crystal panel or an organic Electro Luminescence (EL) panel uses UV curable resin as an adhesive. Additionally, a UV curable ink that is cured by UV irradiation is used as an ink for sheet-fed offset printing. A UV light illuminating apparatus is used to cure such a UV curable ink or UV curable resin. As above, various types of light emitting devices are used, and among them, recently, light emitting devices using LED as a light source are mainly used from the perspective of lower power consumption, a longer service life, and smaller size.

With regard to a light emitting device using LED, for example, Japanese Patent Publication No. 2010-199005 (Patent Literature 1) discloses an LED module comprising first main and sub terminals for connection to an external circuit formed near the first side of the insulating substrate, second main and sub terminals for connection to an external circuit formed near the second side opposite to the first side of the insulating substrate 2, three or more connecting wires formed on the insulating substrate for connecting LEDs continuously aligned at a distance from each other in series, LEDs individually connected between the connecting wires adjacent to each other and connected in series in a same direction (see [abstract]).

RELATED LITERATURES

Patent Literatures (Patent Literature 1) Japanese Patent Publication No. 2010-199005

DISCLOSURE

Technical Problem

The specification required for a light illuminating apparatus varies depending on products on which the light illuminating apparatus is mounted. By this reason, when there is no ready-made power device suitable for the specification of a light illuminating apparatus, development of a new power device or adoption of a ready-made power device with over performance has been made.

However, development of a new power device causes a long product development period and an increased product development cost. Meanwhile, a ready-made product with over performance causes an increased manufacturing cost of a final product. Accordingly, there is a need for technology for easily manufacturing a light illuminating apparatus suitable for the performance of a power device.

To solve the problem such as the foregoing, this disclosure is directed to providing technology for easily manufacturing a light illuminating apparatus suitable for the performance of a power device.

Technical Solution

A light emitting device according to a certain embodiment includes a substrate having an anode pattern and a cathode pattern, and at least one light emitting element connected to the anode pattern and the cathode pattern. The substrate has a connecting part at each of two ends of the anode pattern extending in a connection direction with other light emitting device that is different from the light emitting device to connect the light emitting device to other light emitting device, and a connecting part at each of two ends of the cathode pattern extending in the connection direction to connect the light emitting device to other light emitting device.

By the above configuration, the light emitting device may be electrically connected to other light emitting device in series and in parallel. By this reason, a light illuminating apparatus using this light emitting device may easily change the specification (for example, the rated current value and the rated voltage value) by adjusting a connection relationship between light emitting devices. Thus, manufacturers may easily manufacture a light illuminating apparatus suitable for the existing power device.

Additionally, the cathode pattern is preferably formed in a direction perpendicular to the connection direction with other light emitting device with respect to the anode pattern. A light illuminating apparatus including this light emitting device may shift the series connection and parallel connection only by connecting the connecting part of the light emitting device to a connecting part of other adjacent light emitting device.

Additionally, the substrate preferably includes multiple light emitting elements electrically connected to each other in parallel. A light illuminating apparatus including this light emitting device may suppress the sum of forward direction voltages.

Additionally, the substrate is rectangular, and the connection direction with other light emitting device is a lengthwise direction of the substrate. Each of the multiple light emitting elements is placed at a widthwise direction center of the substrate. A light illuminating apparatus including this light emitting device may suppress non-uniformity of light illumination intensity.

In the light emitting device, the light emitting element includes a light emitting diode (LED) element. In this case, each of the multiple LED elements is preferably configured such that non-uniformity of forward direction voltage is 0.2V or less. More preferably, each of the multiple LED elements is configured such that non-uniformity of forward direction voltage is 0.1V or less. Even more preferably, each of the multiple LED elements is configured such that non-uniformity of forward direction voltage is 0.05V or less. The light emitting device according to this configuration and a light illuminating apparatus including this light emitting device may suppress non-uniformity of light illumination intensity.

Additionally, the LED element includes an anode electrode, and a cathode electrode placed in a vertical direction of the substrate with respect to the anode electrode. The anode electrode is connected to the anode pattern. The cathode electrode is connected to the cathode pattern.

Additionally, the LED element includes an anode electrode, and a cathode electrode placed in an approximately horizontal direction of the substrate with respect to the anode electrode. The anode electrode is connected to the anode pattern. The cathode electrode is connected to the cathode pattern.

Additionally, the connecting part includes a screw hole. Thus, manufacturers may easily establish a connection of the light emitting device and other light emitting device.

According to another embodiment, there is provided a light illuminating apparatus including multiple light emitting devices described above. In the light illuminating apparatus, the multiple light emitting devices include a first light emitting device and a second light emitting device adjacent to the first light emitting device. The connecting part installed on the cathode pattern of the first light emitting device and the connecting part installed on the anode pattern of the second light emitting device are electrically connected. In this case, the first light emitting device and the second light emitting device are electrically connected to each other in series.

Additionally, in the light illuminating apparatus, the connecting part installed on the anode pattern of the first light emitting device and the connecting part installed on the anode pattern of the second light emitting device are electrically connected. The connecting part installed on the cathode pattern of the first light emitting device and the connecting part installed on the cathode pattern of the second light emitting device are electrically connected. In this case, the first light emitting device and the second light emitting device are electrically connected to each other in parallel.

Additionally, the light illuminating apparatus is preferably configured such that non-uniformity of forward direction voltage of the LED element placed in the first light emitting device and forward direction voltage of the LED element placed in the second light emitting device is 0.2V or less. More preferably, the light illuminating apparatus is configured such that non-uniformity of forward direction voltage of them is 0.1V or less. Even more preferably, the light illuminating apparatus is configured such that non-uniformity of forward direction voltage of them is 0.05V or less. The light illuminating apparatus according to this configuration may suppress non-uniformity of light illumination intensity.

Additionally, in the light illuminating apparatus, the second light emitting device is placed in an arrangement direction of the multiple light emitting elements included in the first light emitting device with respect to the first light emitting device. The light illuminating apparatus is configured such that an interval between a light emitting element placed in a closest position to the second light emitting device among the multiple light emitting elements included in the first light emitting device and a light emitting element placed in a closest position to the first light emitting device among the multiple light emitting elements included in the second light emitting device is equal to an interval between adjacent light emitting elements among the multiple light emitting elements included in the first light emitting device. By this configuration, an interval between adjacent light emitting elements is equal all over the light illuminating apparatus. By this reason, the light illuminating apparatus may suppress non-uniformity of light illumination intensity.

Advantageous Effects

The light emitting device according to a certain embodiment is configured to arbitrarily shift the connection condition with other light emitting device between series connection and parallel connection. By this reason, a light illuminating apparatus using the light emitting device may easily change the required current value and voltage value (i.e., easily adapted to the performance of a power device) by shifting the connection condition between light emitting devices.

BEST MODE

Hereinafter, a light emitting device and a light illuminating apparatus according to embodiments will be described in detail with reference to the accompanying drawings. In the following description, like reference symbols are affixed to like components. Their names and functions are also the same. Accordingly, their detailed description is not repeated. Additionally, each embodiment and each variation described below may be properly selectively combined.

(Configuration of an Inspection Apparatus 1)

Figure 1:
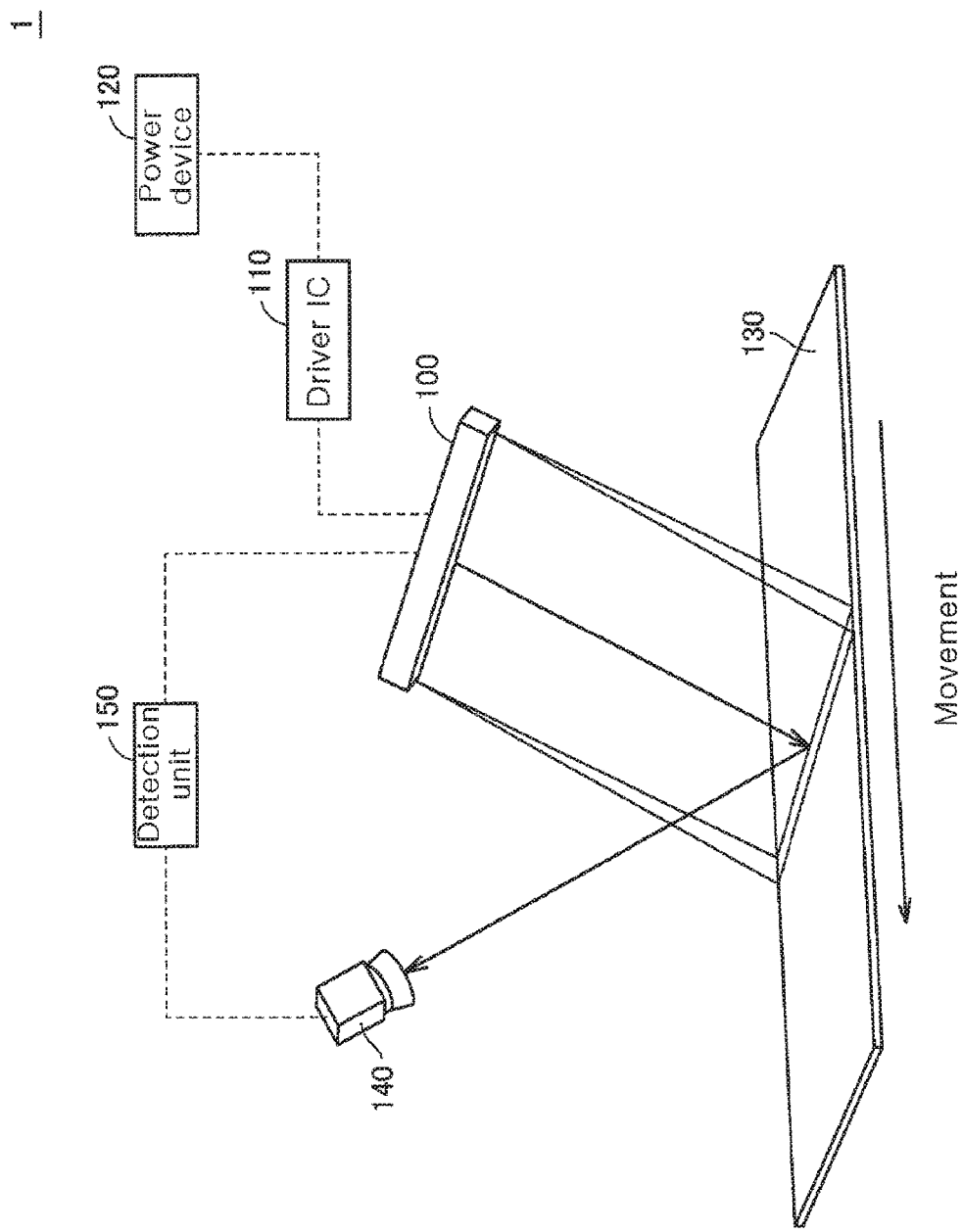
FIG. 1 is a diagram showing configuration of an inspection apparatus 1.

FIG. 1 shows the configuration of the inspection apparatus 1. The inspection apparatus 1 has a light illuminating apparatus 100 including a light emitting device (for example, a light emitting diode (LED) module M as described below) according to a certain embodiment. In addition to the light illuminating apparatus 100, the inspection apparatus 1 further has a driver IC 110, a power device 120, a camera 140, and a detection unit 150. The inspection apparatus 1 detects a surface shape (texture) of an object 130 of inspection.

The driver IC 110 efficiently supplies power from the power device 120 to the light illuminating apparatus 100. The driver IC 110 includes, for example, a boost chopper circuit, and supplies necessary power to the light illuminating apparatus 100 by a Pulse Width Modulation (PWM) method. Additionally, the driver IC 110 may include a circuit such as an overvoltage protection circuit that stops working when voltage applied to the light illuminating apparatus 100 exceeds a preset voltage value.

As shown in FIG. 1, the light illuminating apparatus 100 is configured to irradiate line light onto a target surface of the object 130 of inspection moving in horizontal direction, the line light extending in the shape of a straight line in a direction (a widthwise direction perpendicular to the irradiation direction) perpendicular to the movement direction of the object 130 of inspection. The configuration of the light illuminating apparatus 100 is described in detail using FIGS. 2-4.

The object 130 of inspection is made of, for example, aluminum, stainless steel, rolled steel, a material of a silicon substrate or a glass substrate, and has a mirror-like target surface by polishing or plastic machining, from which light (incident light) can be reflected. The line light is reflected from the target surface and is incident on the camera 140.

The camera 140 includes, for example, multiple Charge Coupled Devices (CCDs). The camera 140 is placed in a location of line symmetry with the light illuminating apparatus 100 with respect to the normal line of the target surface, and captures an image of the line light regularly reflected from the target surface. The camera 140 outputs the acquired image data to the detection unit 150.

The detection unit 150 includes, for example, a processor, and a memory device into which a control program is loaded. In this case, the processor reads and executes the control program to detect the surface condition of the target surface (the texture condition of the surface) from the inputted image data. More specifically, the processor calculates a surface angle of the target surface from the image data, and evaluates the texture condition (surface roughness) of the target surface by integrating the surface angle.

Additionally, although an example of the light illuminating apparatus 100 used in the inspection apparatus 1 is described above, the usage example of the light illuminating apparatus 100 is not limited thereto. The light illuminating apparatus 100 may be used in any apparatus that irradiates visible light, ultraviolet light and infrared light. For example, the light illuminating apparatus 100 may be configured to irradiate visible light, and may be used in liquid crystal display backlights, lighting for plant growth, medical lighting such as endoscopy, and other applications. Additionally, the light illuminating apparatus 100 may be configured to irradiate ultraviolet light, and may be used in curing of an ultraviolet curable ink or ultraviolet curable resin, pest control, photolithography, sterilization, deletion of recordings in Erasable Programmable Read Only Memory (EPROM), and other applications.

(Configuration of the Light Illuminating Apparatus 100)

Figure 2:
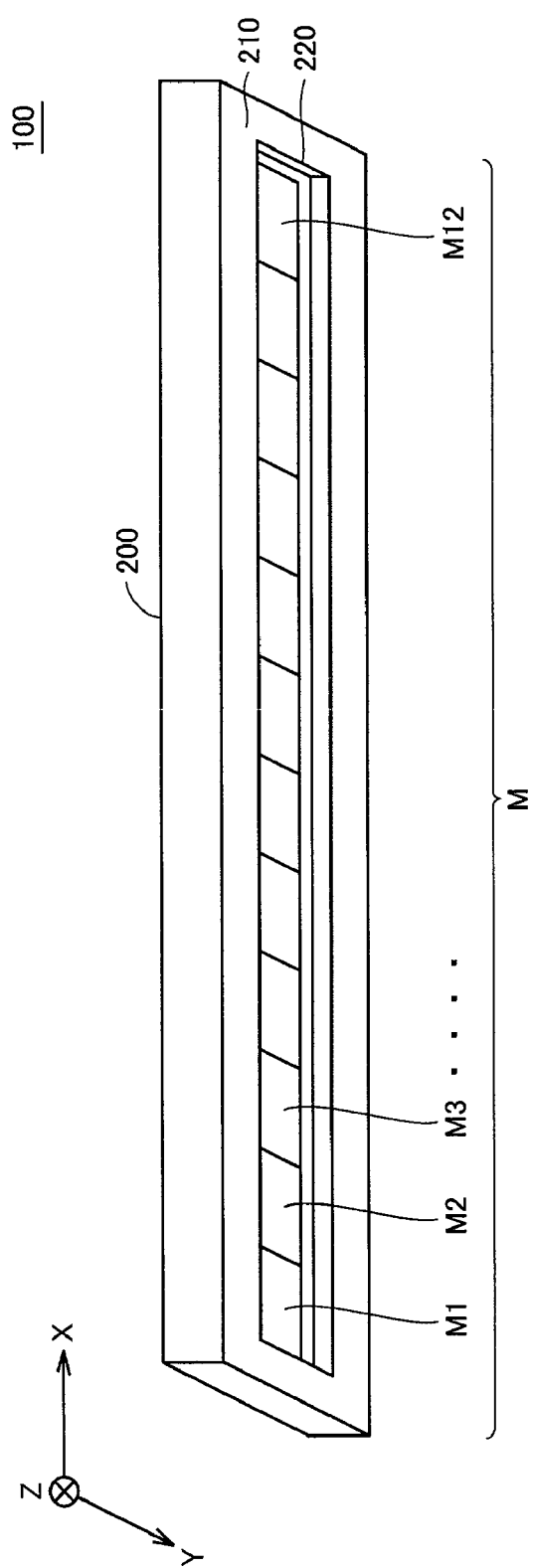
FIG. 2 is a diagram showing a configuration example of a light illuminating apparatus 100 according to a certain embodiment.

FIG. 2 shows a configuration example of the light illuminating apparatus 100 according to a certain embodiment. As shown in FIG. 2, the light illuminating apparatus 100 has a housing 200 of a long rectangular shape in widthwise direction (X direction) of the object 130 of inspection. Multiple LED modules M1, M2, . . . , M12 are placed in a recess of a surface 210 of the housing 200 facing the object 130 of inspection. Additionally, a light emitting window 220 that covers the multiple LED modules M1, M2, . . . , M12 is installed on the surface 210. Hereinafter, the LED modules M1, M2, . . . are referred collectively to as ⌈LED module $M_j$⌋. The LED module M acts as a light emitting device.

(Configuration of the LED Module M)

Figure 3:
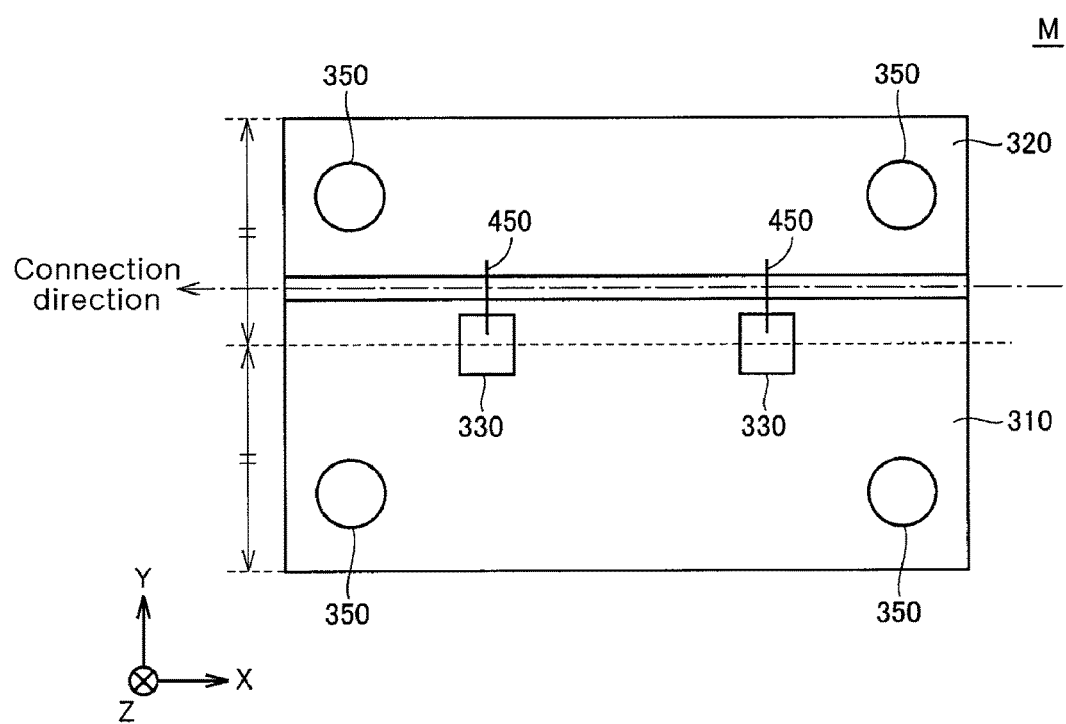
FIG. 3 is a diagram showing a configuration example of a light emitting diode (LED) module M according to a certain embodiment.

FIG. 3 shows a configuration example of the LED module M according to a certain embodiment. Referring to FIG. 3, the LED module M has an anode pattern 310 and a cathode pattern 320 on a substrate 410 described below. More specifically, the cathode pattern 320 is formed in a direction (Y direction) perpendicular to the connection direction (X direction) of adjacent LED modules M with respect to the anode pattern 310. The anode pattern 310 and the cathode pattern 320 may be formed by, for example, a copper foil. The anode pattern 310 and the cathode pattern 320 formed on the same LED module M do not contact each other.

The LED module M according to a certain embodiment has an LED chip 330 (an LED element) connected to the anode pattern 310 and the cathode pattern 320. In the example shown in FIG. 3, the LED chip 330 is placed on the anode pattern 310, and is connected to the cathode pattern 320 through a bonding wire 450. Additionally, in the example shown in FIG. 3, two LED chips 330 are placed on the same LED module M. These LED chips 330 are electrically connected to each other in parallel. In the LED module M, a placement position of each of the multiple LED chips 330 may be a center of the LED module M (the substrate 410) in a direction (Y direction) perpendicular to the connection direction (X direction). In other words, a placement position of each of the multiple LED chips 330 may be a center in widthwise direction (Y direction) perpendicular to the lengthwise direction (connection direction) of the rectangular LED module M (the substrate 410). Thus, non-uniformity of light illumination intensity of the light illuminating apparatus 100 is suppressed. The reason is described below using FIG. 5.

In a certain embodiment, each of the multiple LED chips 330 is configured such that non-uniformity of forward direction voltage is 0.2V or less. The reason is that non-uniformity of light illumination intensity of the LED module M and non-uniformity of light illumination intensity of the light illuminating apparatus 100 is suppressed. In another embodiment, to further suppress the non-uniformity of light illumination intensity, each of the multiple LED chips 330 is configured such that non-uniformity of forward direction voltage is 0.1V or less. In still another embodiment, each of the multiple LED chips 330 is configured such that non-uniformity of forward direction voltage is 0.05V or less.

Additionally, the LED module M has a connecting part 350 for connection to other LED module M at the four corners. In other words, the LED module M has a connecting part 350 for connection to other LED module M at each of the two ends of the anode pattern 310 and the cathode pattern 320 extending in the connection direction (X direction) with other LED module M. In a certain embodiment, the connecting part 350 may be a hole into which a screw is inserted. When a screw is inserted into the connecting part 350 and passes through it, the LED module M is fixed to the surface 210 of the housing 200. Preferably, the four connecting parts 350 are placed in point symmetry with respect to the normal line that passes through a geometric center of the exterior shape of the module M. As described below, the LED module M may be rotated 180° and connected to other LED module M (series connection), and may be connected to other LED module M without rotation (parallel connection). As the multiple connecting parts 350 are placed in point symmetry, the centers of two LED modules M connected by any connection method in Y direction are placed on a straight line. That is, as the multiple connecting parts 350 are placed in point symmetry, minimization of the light illuminating apparatus 100 may be achieved.

In addition, although in the above example, the light illuminating apparatus 100 employs the LED module M having the LED chip as the light emitting device, a module with a laser diode may be employed. Additionally, in this case, the light illuminating apparatus 100 may further have a cylindrical lens that converges light emitted from the laser diode and changes it to a laser light of line shape. Subsequently, the configuration and connection relationship of the LED chip 330 will be described.

(Configuration of the LED Chip 330)

Figure 4A:
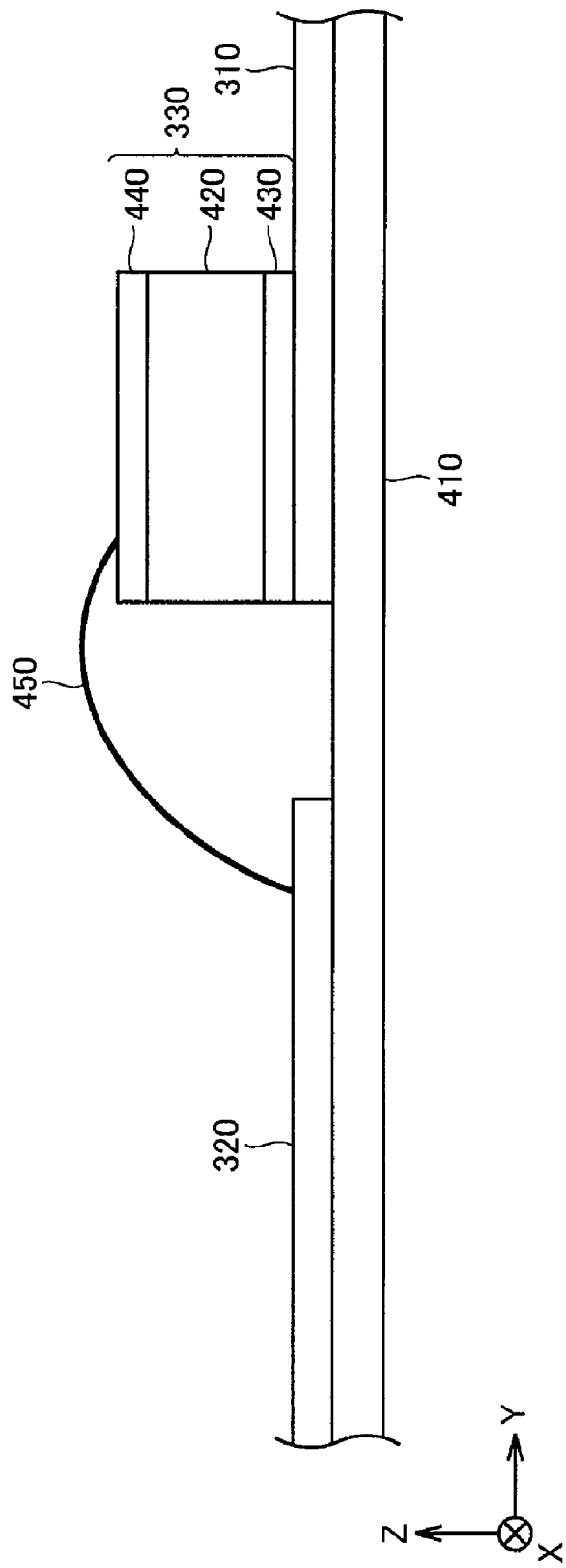
FIGS. 4A and 4B are diagrams showing a configuration example and a connection relationship example of an LED chip 330 according to a certain embodiment.
Figure 4B:
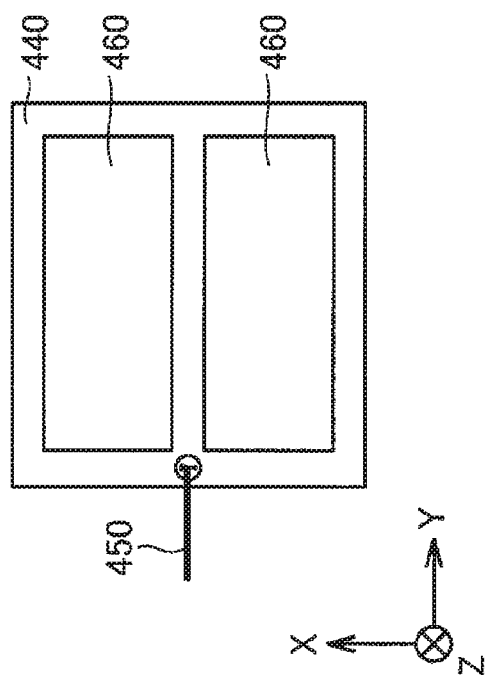

FIGS. 4A and 4B show a configuration example and a connection relationship example of the LED chip 330 according to a certain embodiment. FIG. 4A is a diagram of the neighborhood of the LED chip 330 of the LED module M when viewed in X-axis direction. FIG. 4B is a diagram of the neighborhood of the LED chip 330 of the LED module M when viewed in Z-axis direction. The LED chip 330 has a semiconductor layer 420, an anode electrode 430, and a cathode electrode 440. The cathode electrode 440 is placed in vertical direction of the substrate 410 with respect to the anode electrode 430 with the semiconductor layer 420 interposed between. The anode electrode 430 is connected to the anode pattern 310. A conductive die bond is formed between the anode electrode 430 and the anode pattern 310 to bring them into close contact. The cathode electrode 440 is connected to the cathode pattern 320 through the bonding wire 450. Accordingly, the LED chip 330 shown in FIGS. 4A and 4B is a so-called vertical-type chip in which an electric current flows in vertical direction (Z direction) of the substrate 410. The substrate 410 of the LED module M having the vertical-type LED chip is formed by, for example, conductive aluminum nitride ceramics.

As shown in FIG. 4B, the cathode electrode 440 is formed on an outer circumferential part and a central part of an upper surface (XY plane) of the semiconductor layer 420. By this reason, two areas 460 of the upper surface of the semiconductor layer 420 are exposed. The semiconductor layer 420 has a P-type semiconductor layer (not shown) formed on the side of the anode electrode 430, an N-type semiconductor layer (not shown) formed on the side of the cathode electrode 440, and a light emitting layer (not shown) formed between the P-type semiconductor layer and the N-type semiconductor layer. When an electric current is applied between the anode electrode 430 and the cathode electrode 440, light is produced from the light emitting layer and irradiated from the light emitting window 220 installed on the surface 210 of the housing 200 through the areas 460.

Additionally, although not particularly shown, the LED module M may further have a reflection plate for increasing light emission efficiency, encapsulation resin for improving stability or others in the neighborhood of the LED chip 330.

(Connection Relationship Between the LED Modules M)

Figure 5:
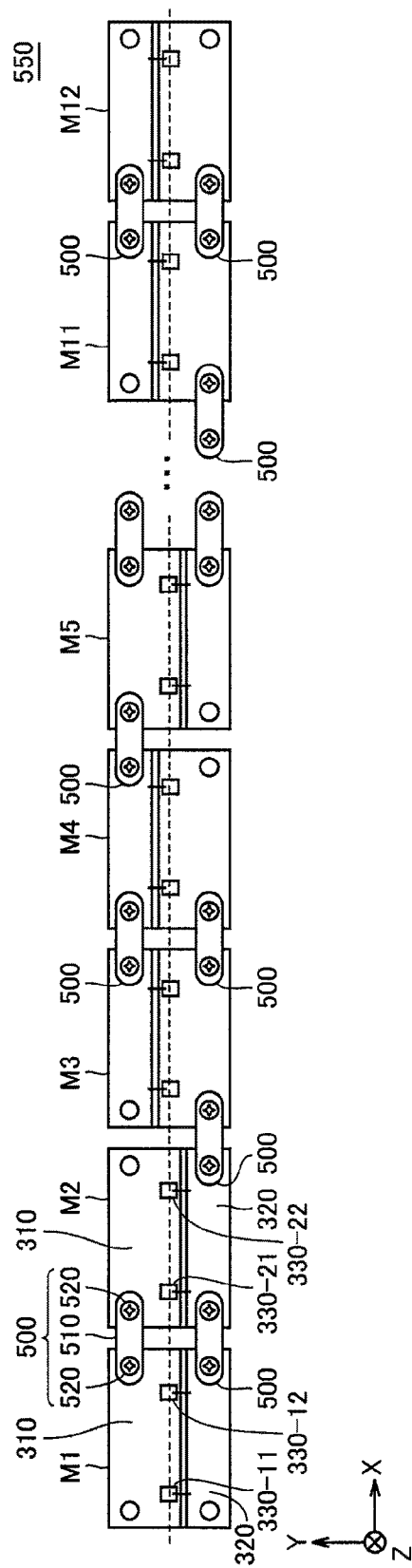
FIG. 5 is a diagram illustrating a connection condition of an LED module M and other LED module M.
Figure 6:
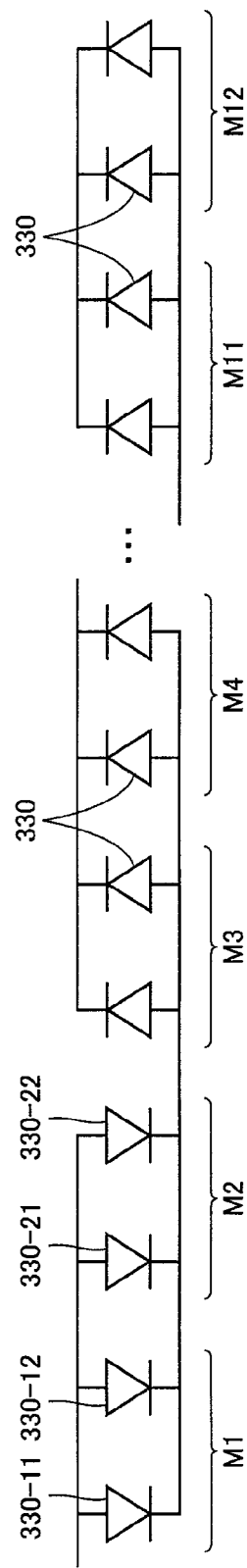
FIG. 6 is a diagram showing an equivalent circuit of the light illuminating apparatus 100 shown in FIG. 5.

FIG. 5 is a diagram illustrating a connection condition of the LED module M and other LED module M. FIG. 6 shows an equivalent circuit of an LED assembly 550 shown in FIG. 5. As shown in FIG. 5, a connection member 500 electrically connects the LED module M to other LED module. The connection member 500 includes, for example, a conductive bridge member 510 and a screw 520. The bridge member 510 includes, for example, a copper plate with a hole formed at each of two ends in lengthwise direction (X direction in FIG. 5). In a state that the hole formed in the bridge member 510 and the connecting part 350 (screw hole) formed in the LED module M overlap, when the screw 520 is inserted into and passes through these holes, the LED modules M are connected to each other.

In this instance, an inter-chip distance between adjacent chips of all the LED chips 330 included in the LED assembly 550 is equal. That is, an interval between adjacent LED chips 330 placed on an LED module M is equal to an interval between an LED chip 330 placed in a closest position to the LED module M on the other side adjacent to the corresponding LED module M among the multiple LED chips 330 included in the LED module M on one side, and an LED chip 330 placed in a closest position to the LED module M on one side among the multiple LED chips 330 included in the LED module M on the other side. As a specific example, an interval between an LED chip 330-11 and an LED chip 330-12 of FIG. 5 is equal to an interval between the LED chip 330-12 and an LED chip 330-21. According to this configuration, an interval between adjacent LED chips 330 is equal all over the light illuminating apparatus 100. Thus, non-uniformity of light illumination intensity of the light illuminating apparatus 100 is suppressed.

The connection condition of the LED module M1 and the LED module M2 is described. Referring to FIG. 5, the anode pattern 310 of the LED module M1 and the anode pattern 310 of the LED module M2 are electrically connected by the connection member 500. Additionally, the cathode pattern 320 of the LED module M1 and the cathode pattern 320 of the LED module M2 are electrically connected by the connection member 500. That is, the LED module M1 and the LED module M2 are electrically connected to each other in parallel. By this reason, as shown in FIG. 6, four LED chips 330-11, 330-12, 330-21, 330-22 placed on the LED modules M1 and M2 are electrically connected to each other in parallel. Referring again to FIG. 5, the connection condition of the LED module M3 and the LED module M4 is the same as the connection condition of the LED module M1 and the LED module M2.

In a certain embodiment, the light illuminating apparatus 100 is configured such that non-uniformity of forward direction voltage of each of the LED chips 330 (four LED chips 330) electrically connected to each other in parallel is 0.2V or less. The reason is that non-uniformity of light illumination intensity of the light illuminating apparatus 100 composed of the multiple LED modules M may be suppressed. In another embodiment, to further suppress the non-uniformity of light illumination intensity, the light illuminating apparatus 100 is configured such that non-uniformity of forward direction voltage of each of the LED chips 330 connected in parallel is 0.1V or less. In still another embodiment, the light illuminating apparatus 100 is configured such that non-uniformity of forward direction voltage of each of the LED chips 330 connected in parallel is 0.05V or less.

Subsequently, the connection condition of the LED module M2 and the LED module M3 is described. The cathode pattern 320 of the LED module M2 and the anode pattern 310 of the LED module M3 are electrically connected by the connection member 500. That is, the LED module M2 and the LED module M3 are electrically connected to each other in series. By this reason, as shown in FIG. 6, four LED chips 330 placed on the LED modules M1 and M2 and four LED chips 330 placed on the LED modules M3 and M4 are electrically connected to each other in series. Additionally, the LED module M3 connected to the LED module M2 in series is placed in 180° rotated position about the normal line of the substrate 410 with respect to the LED module M2. More specifically, the LED module M3 is placed in 180° rotated position (in point symmetry) about the normal line that passes through a geometric center of the exterior shape of the substrate 410 on the XY plane with respect to the LED module M2.

The foregoing describes that a placement position of each of the multiple LED chips 330 mounted on the LED module M is a center in Y direction of the substrate 410, thereby suppressing non-uniformity of light illumination intensity of the light illuminating apparatus 100. This is because the position in Y direction is the same for each of the multiple LED chips 330 placed on the light illuminating apparatus 100 no matter when the LED modules M are connected in parallel or in series.

Additionally, the foregoing describes that the cathode pattern 320 is formed in a direction (Y direction) perpendicular to the connection direction (X direction) of adjacent LED modules M with respect to the anode pattern 310. By the corresponding configuration, the connection condition of the LED module M and other adjacent LED module M may be easily shifted only by connecting the connecting parts 350 of these LED modules M. If in the LED module M, the cathode pattern 320 is formed in the connection direction (X direction) of adjacent LED modules M with respect to the anode pattern 310, only one of the anode pattern 310 and the cathode pattern 320 of the LED module M is adjacent to the other LED module M. By this reason, in this case, it is impossible to connect the LED modules M in parallel only by connecting the adjacent connecting parts 350. For example, in case that the rated forward direction current If of the LED chip 330 is 100 mA and forward direction voltage Vf is 3V, when the light illuminating apparatus 100 includes six blocks connected in series, each block including four LED chips 330 connected to each other in parallel, the rated current value of the light illuminating apparatus 100 is 400 mA and the sum of forward direction voltages is 18V.

Figure 7:
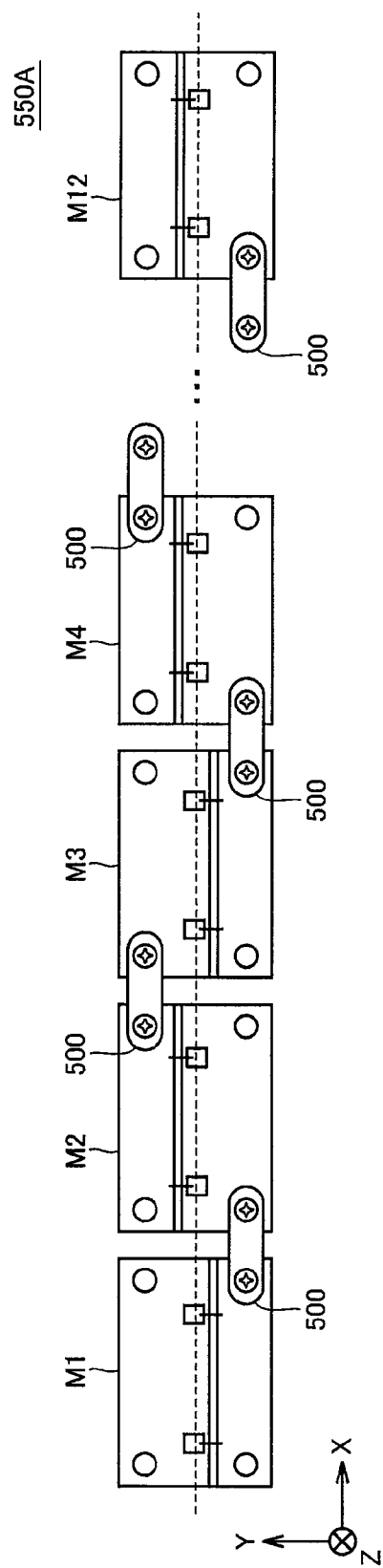
FIG. 7 is a diagram showing configuration of an LED assembly 550A.
Figure 8:
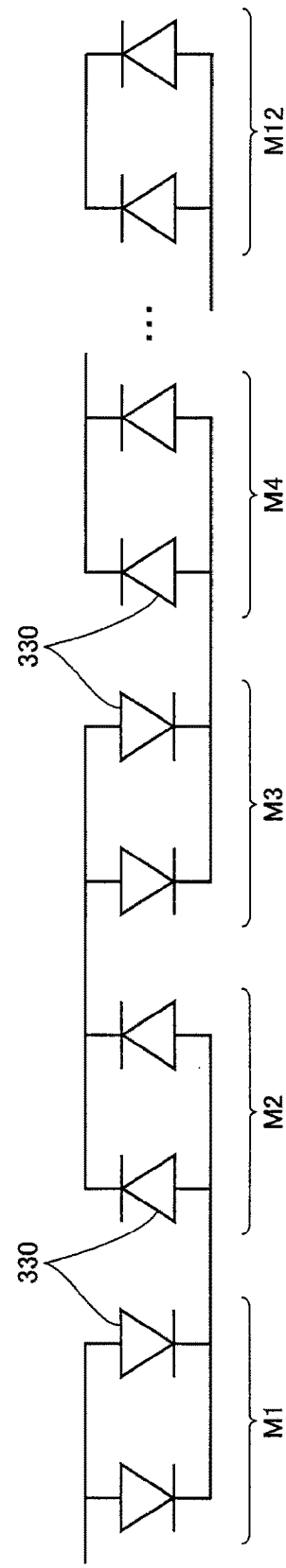
FIG. 8 is a diagram showing an equivalent circuit of the LED assembly 550A shown in FIG. 7.

FIG. 7 shows configuration of an LED assembly 550A. Additionally, the LED assembly 550A has the same configuration as the LED assembly 550 described in FIG. 5 except the connection relationship between the LED modules M. This condition is the same for LED assemblies 550B and 550C described below. FIG. 8 shows an equivalent circuit of the LED assembly 550A shown in FIG. 7.

In an example shown in FIGS. 7 and 8, adjacent LED modules M are electrically connected to each other in series. In this case, the LED assembly 550A includes twelve blocks connected in series, each block including two LED chips 330 connected to each other in parallel. In this case, the rated current value of the LED assembly 550A is 200 mA, and the rated voltage value is 36V.

Figure 9:
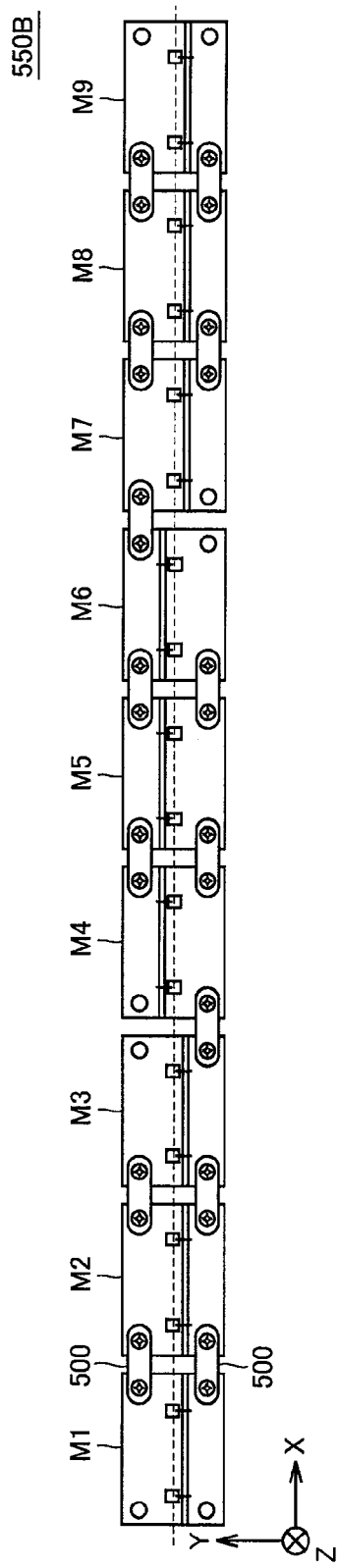
FIG. 9 is a diagram showing configuration of an LED assembly 550B.
Figure 10:
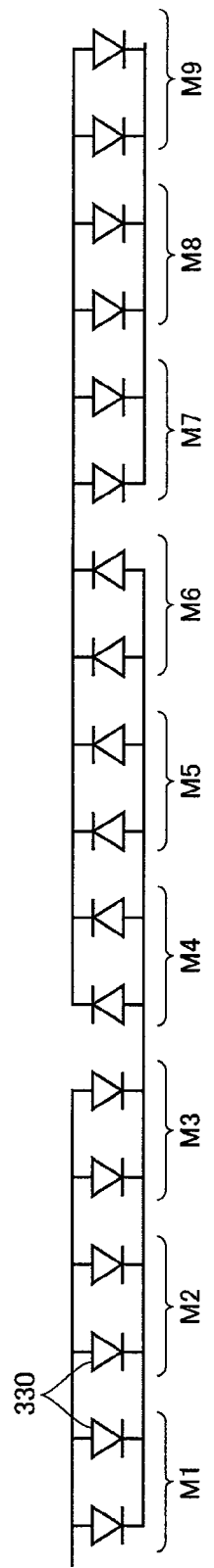
FIG. 10 is a diagram showing an equivalent circuit of the LED assembly 550B shown in FIG. 9.

FIG. 9 shows configuration of an LED assembly 550B. FIG. 10 shows an equivalent circuit of the LED assembly 550B shown in FIG. 9. In an example shown in FIGS. 9 and 10, the LED assembly 550B includes three blocks connected in series, each block including six LED chips 330 connected to each other in parallel. In this case, the rated current value of the LED assembly 550B is 600 mA, and the rated voltage value is 9V.

As described above, when the anode patterns 310 and the cathode patterns 320 of the LED module M and other adjacent LED module M are each connected to each other, they are electrically connected in parallel. Additionally, when the anode pattern 310 of the LED module M on one side and the cathode pattern 320 of adjacent LED module M on the other side are connected, they are electrically connected in series. In other words, the LED module M (light emitting device) is configured to arbitrarily shift the connection condition with other LED module M between series connection and parallel connection. By this reason, light illuminating apparatus manufacturers may easily change the current value and voltage value required for the light illuminating apparatus by shifting the connection condition between the LED modules M. Thus, light illuminating apparatus manufacturers may easily manufacture a light illuminating apparatus suitable for the specification of the existing power device. As a result, manufacturers of products (for example, the inspection apparatus 1) having the light illuminating apparatus mounted thereon may achieve the shortened development period of products and reduced manufacturing cost of products.

In addition, each of the multiple LED chips 330 placed on the LED module M is electrically connected to each other in parallel. As a result, because an increase of the rated voltage value of the light illuminating apparatus is prevented, safety of the light illuminating apparatus may be ensured. Additionally, when the rated voltage value of the light illuminating apparatus is low, safety test standards imposed on the light illuminating apparatus are relaxed (for example, the number of test items is reduced). By this reason, manufacturers may further reduce the manufacturing cost of the light illuminating apparatus.

Additionally, when ceramic is used for the substrate of the LED module, it is difficult to obtain a large substrate according to the manufacturing characteristics. The conventional art responded to this problem by driving multiple LED modules using each corresponding driver IC. However, this method is disadvantageous in terms of manufacturing cost and power consumption because as much driver ICs as the number of LED modules are needed. By contrast, the light illuminating apparatus according to an embodiment may arbitrarily adjust the light illumination intensity and light illumination range by combining the multiple LED modules M. Additionally, because the light illuminating apparatus according to an embodiment can drive the multiple LED modules M by one driver IC, manufacturing cost containment and low power consumption may be achieved.

(Variation 1)

In the above example, the light illuminating apparatus is configured such that adjacent LED modules M are all connected in the same direction (X direction), and acts as a line light source. Additionally, the connection direction of the LED modules M is not limited to one direction.

Figure 11:
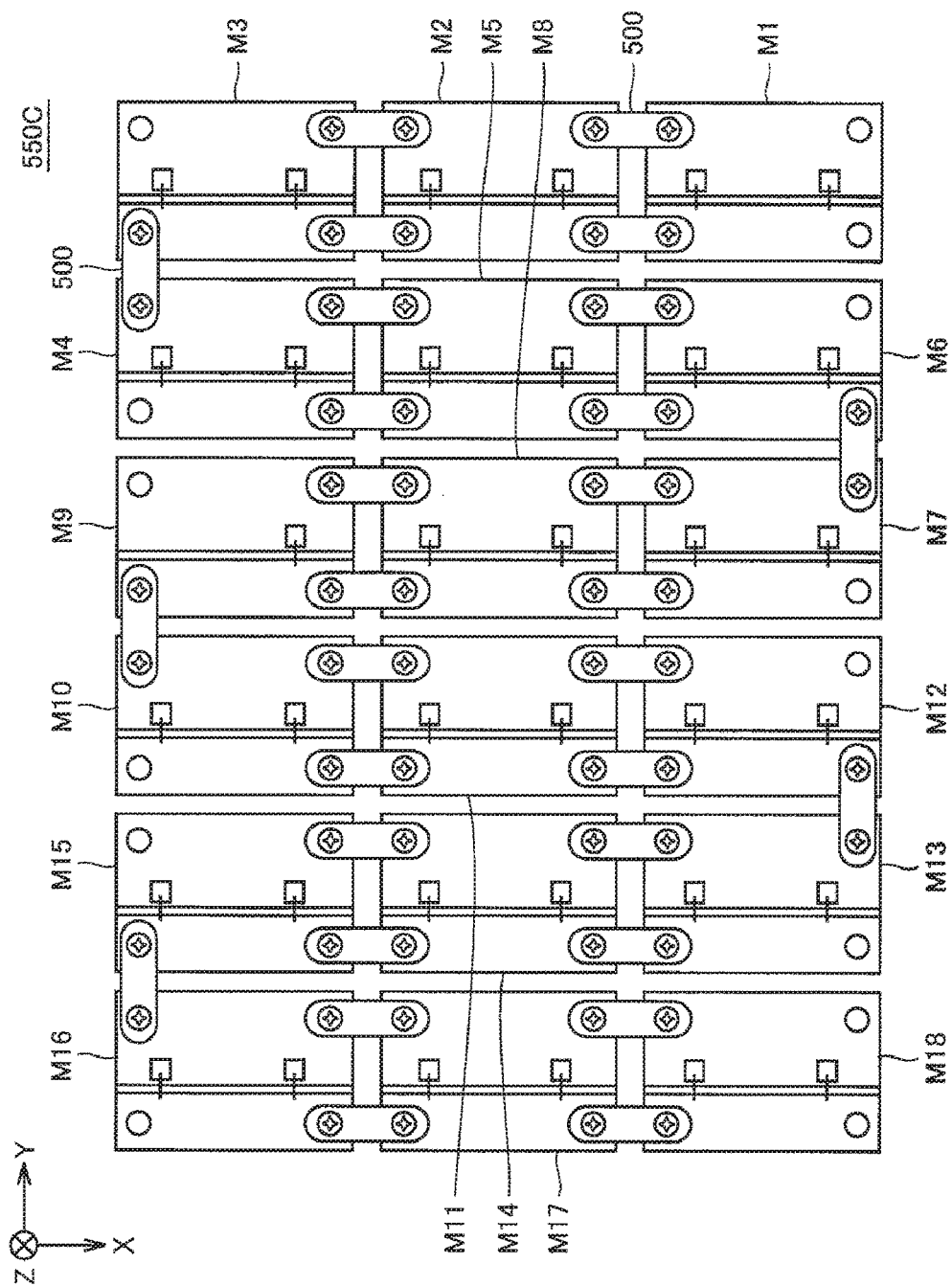
FIG. 11 is a diagram showing configuration of an LED assembly 550C according to variation 1.
Figure 12:
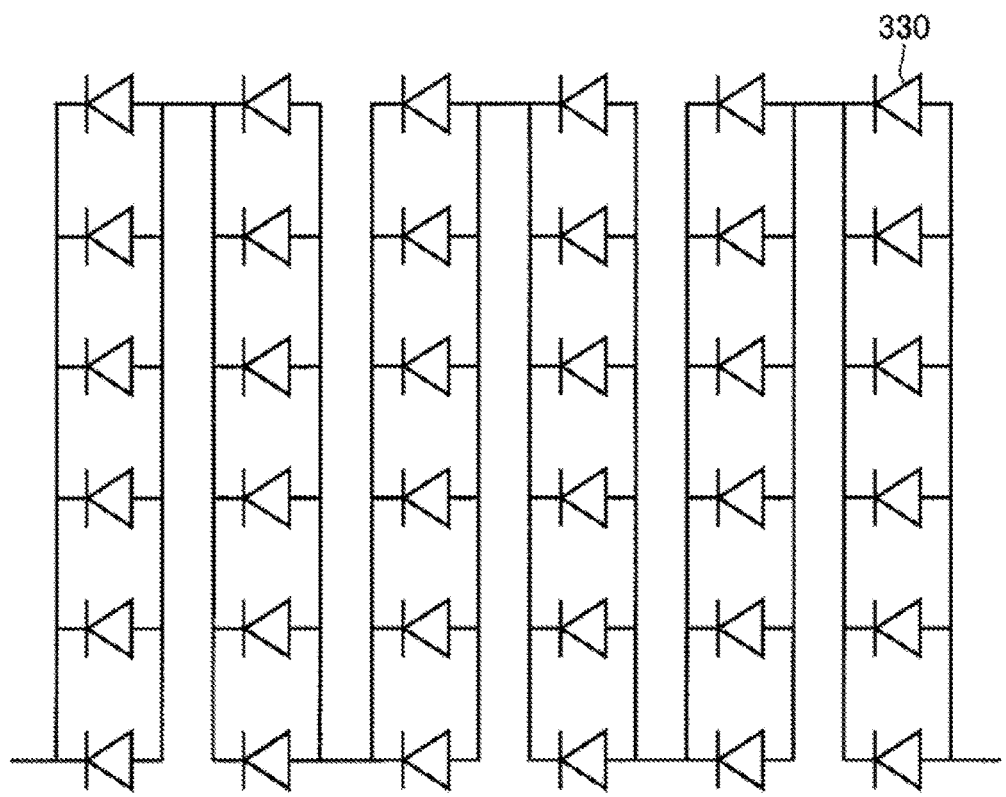
FIG. 12 is a diagram showing an equivalent circuit of the LED assembly 550C shown in FIG. 11.

FIG. 11 shows configuration of an LED assembly 550C according to variation 1. FIG. 12 shows an equivalent circuit of the LED assembly 550C shown in FIG. 11. As shown in FIG. 11, the LED assembly 550C includes six blocks connected in series, each block including three LED modules M electrically connected in parallel. In the LED assembly 550C, the connection direction (Y direction) of the LED modules M connected to each other in series is perpendicular to the connection direction (X direction) of the LED modules M connected to each other in parallel. By this reason, the LED module M4 is placed in Y direction with respect to the LED module M3.

The LED assembly 550C according to the corresponding configuration acts as a surface light source, not a line light source. A light illuminating apparatus using the LED module M according to an embodiment may easily adjust the light illumination intensity and light illumination range by adjusting the number of LED modules M placed in the light illuminating apparatus and a connection relationship between the LED modules M. By this reason, manufacturers may easily manufacture a light illuminating apparatus suitable for the required specification.

(Variation 2)

Although in the above example, the LED module M is configured to have two LED chips 330 placed thereon, the number of LED chips 330 placed is not limited to two.

Figure 13:
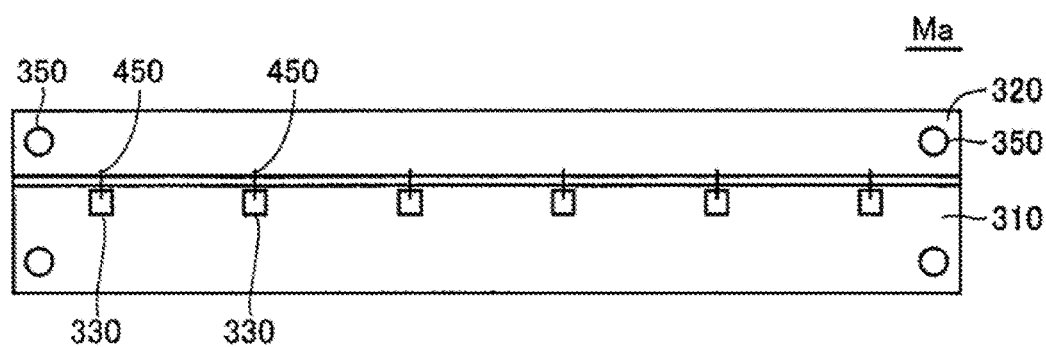
FIG. 13 is a diagram showing configuration of an LED module Ma according to variation 2.

FIG. 13 shows configuration of an LED module Ma according to variation 2. The LED module Ma has six LED chips 330. Each of these six LED chips 330 is electrically connected to each other in parallel. The rated current value of the LED module Ma is 600 mA, and the rated voltage value is 3V (in case that forward direction current If of the LED chip 330 is 100 mA and forward direction voltage Vf is 3V). That is, the rated current value of a light illuminating apparatus composed of a combination of LED modules Ma is at least 600 mA, and the rated voltage value is at least 3V.

Figure 14:
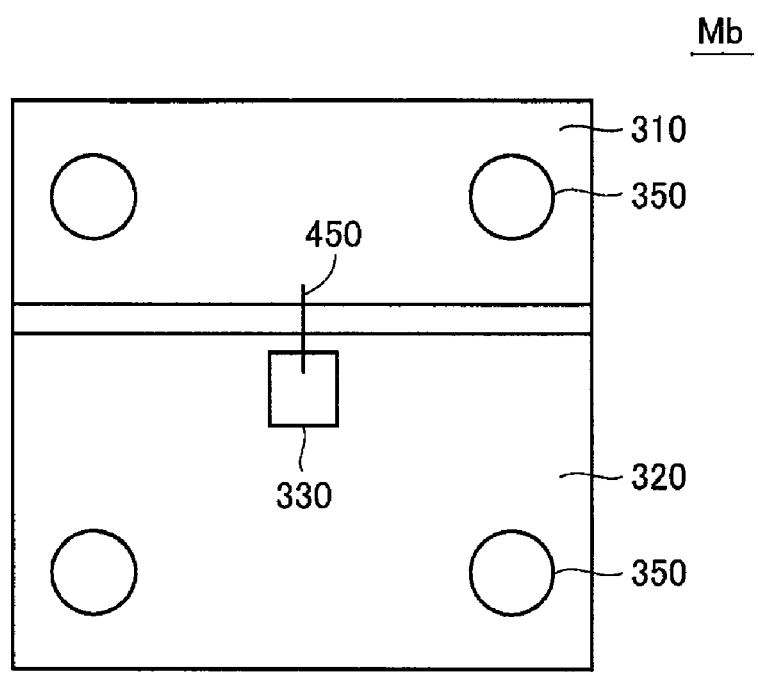
FIG. 14 is a diagram showing configuration of an LED module Mb according to variation 2.

FIG. 14 shows configuration of an LED module Mb according to variation 2. The LED module Mb has one LED chip 330. By this reason, the rated current value of a light illuminating apparatus composed of a combination of LED modules Mb is at least 100 mA, and the rated voltage value is at least 3V (in case that forward direction current If of the LED chip 330 is 100 mA and forward direction voltage Vf is 3V). As described above, as the number of LED chips 330 mounted on the LED module is smaller, the degree of freedom in the specification of the light illuminating apparatus composed of the corresponding LED modules increases. By this reason, the light illuminating apparatus composed of a combination of the LED modules Mb may be adapted to the specification of the power device more suitably.

(Variation 3)

Figure 15:
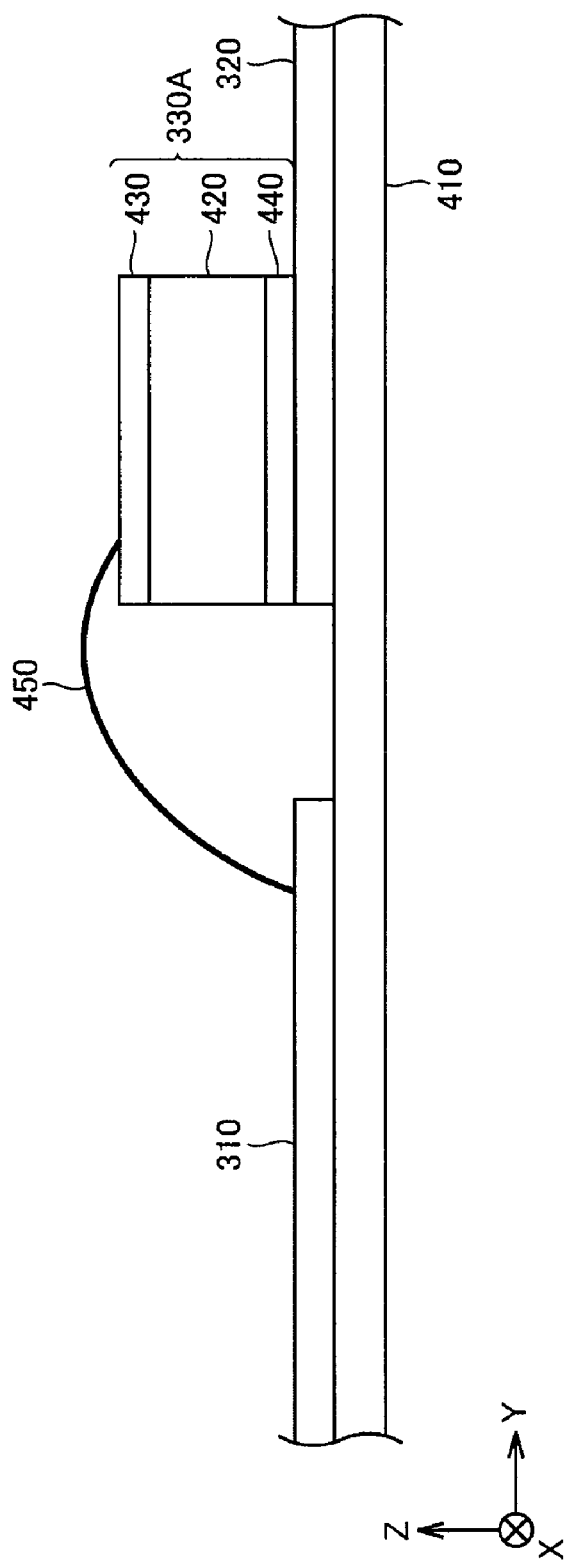
FIG. 15 is a diagram showing configuration and a connection relationship of an LED chip 330A according to variation 3.

FIG. 15 shows configuration and a connection relationship of an LED chip 330A according to variation 3. The LED chip 330A is different from the LED chip 330 in that the semiconductor layer 420, the anode electrode 430 and the cathode electrode 440 are formed on the cathode pattern 320, not on the anode pattern 310. Additionally, in the LED chip 330A, the cathode electrode 440 is connected to the cathode pattern 320. The anode electrode 430 is placed in vertical direction (Z direction) of the substrate 410 with respect to the cathode electrode 440 with the semiconductor layer 420 interposed between. The anode electrode 430 is connected to the anode pattern 310 through the bonding wire 450. Likewise, in case that the LED chip 330A having such configuration is placed on an LED module M, the LED module M and a light illuminating apparatus may realize a series of effects described above.

(Variation 4)

Figure 16:
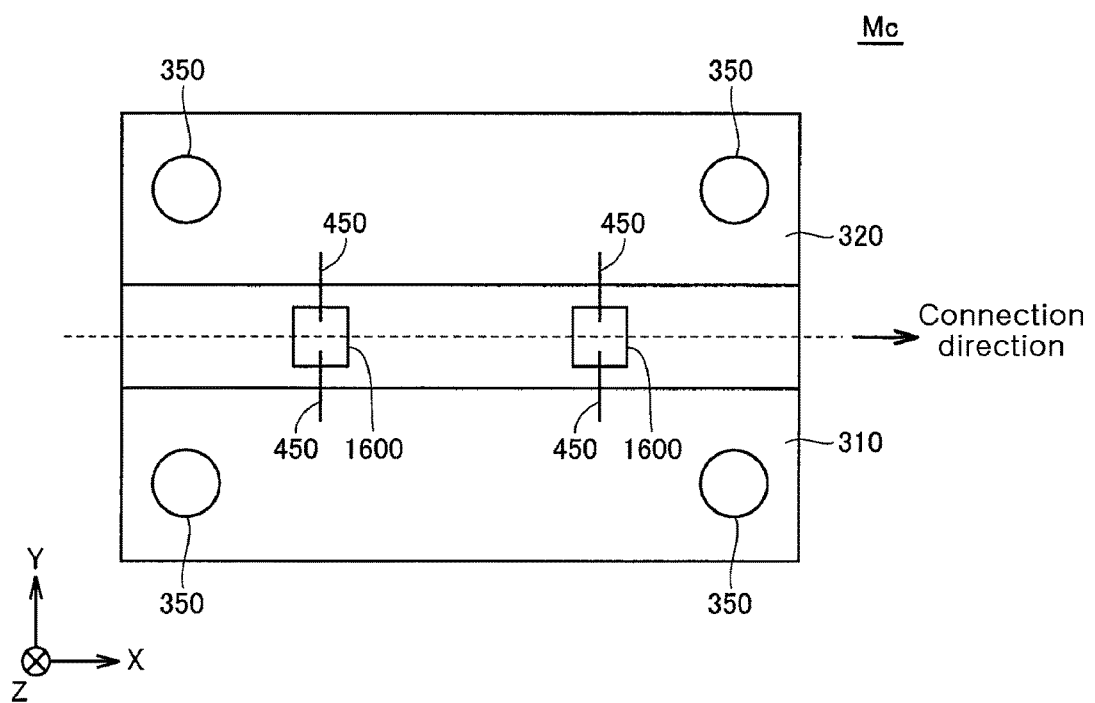
FIG. 16 is a diagram showing configuration of an LED module Mc according to variation 4.

FIG. 16 shows configuration of an LED module Mc according to variation 4. The LED module Mc is different from the LED module M in that the LED module Mc has an LED chip 1600 instead of the LED chip 330. The configuration and connection relationship of the LED chip 1600 are described using FIG. 17.

Figure 17:
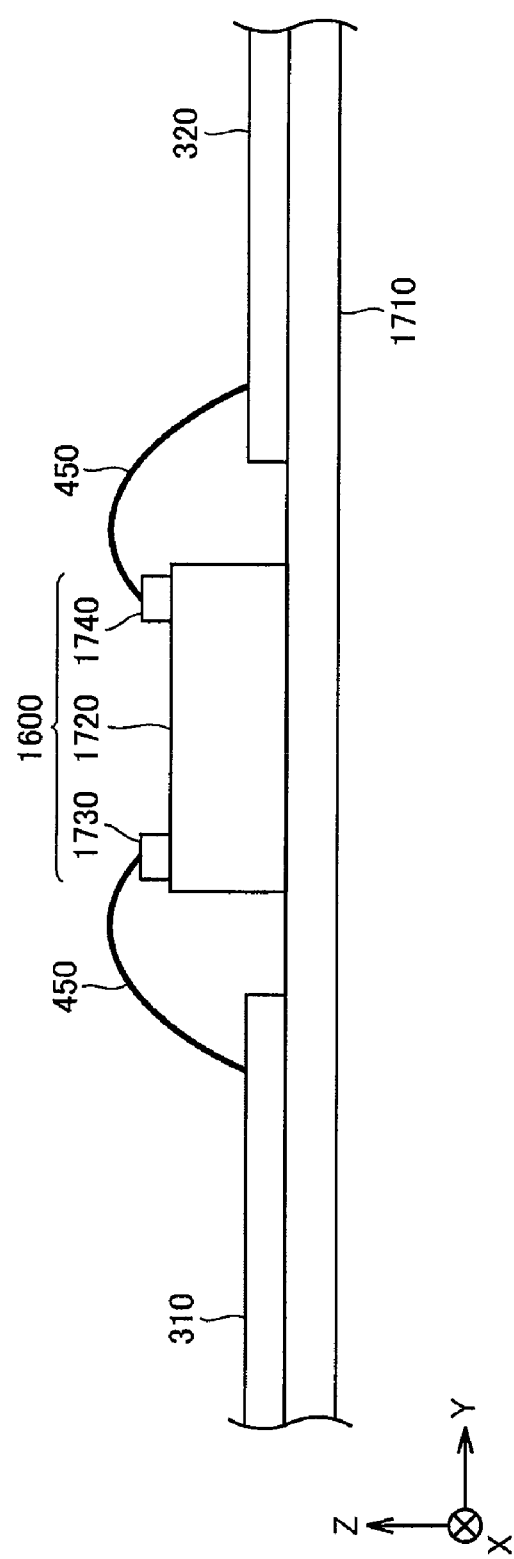
FIG. 17 is a diagram showing configuration and a connection relationship of an LED chip 1600 according to variation 4.

FIG. 17 shows the configuration and connection relationship of the LED chip 1600 according to variation 4. The LED chip 1600 shown in FIG. 17 has a semiconductor layer 1720 and pads 1730 and 1740. The semiconductor layer 1720 is mounted on a substrate 1710. The pads 1730 and 1740 are formed on the semiconductor layer 1720. More specifically, the pad 1730 is formed on a P-type semiconductor layer, and the pad 1740 is formed on an N-type semiconductor layer formed on a side opposite to the P-type semiconductor layer with a light emitting layer interposed between. The pad 1730 is connected to the anode pattern 310 through the bonding wire 450. The pad 1740 is connected to the cathode pattern 320 through the bonding wire 450. In other words, the pad 1730 acts as an anode electrode, and the pad 1740 acts as a cathode electrode. The cathode electrode (the pad 1740) is placed in approximately horizontal direction of the substrate 1710 with respect to the anode electrode (the pad 1730). The LED chip 1600 is a so-called lateral-type chip in which an electric current flows in approximately horizontal direction with respect to the substrate 1710. The substrate 1710 of the LED module having the lateral-type LED chip 1600 is formed by, for example, sapphire with insulating properties. Additionally, in general, the above-described vertical-type LED chip is characterized by high heat radiation and high orientation (high brightness), while this lateral-type LED chip is characterized by light emission in all directions. The LED module Mc and a light illuminating apparatus having the lateral-type LED chip may realize a series of effects described above.

Figure 18:
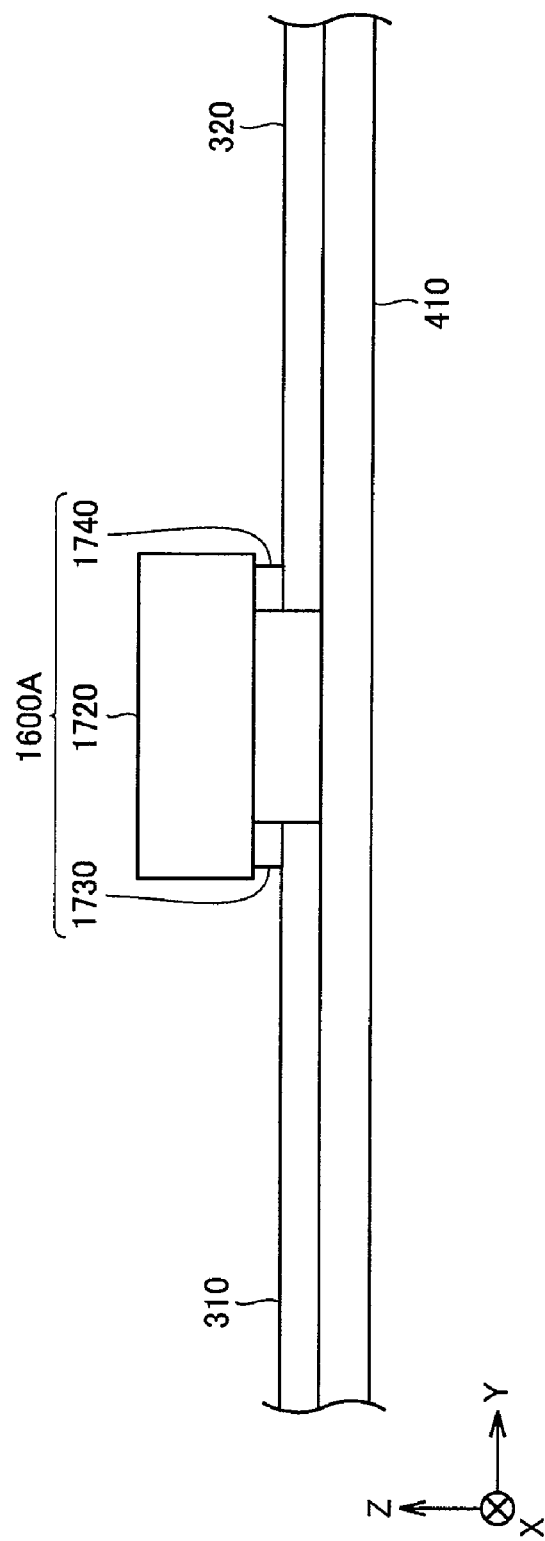
FIG. 18 is a diagram showing configuration and a connection relationship of a flip chip-type LED chip 1600A.

Additionally, as the lateral-type chip, a flip chip-type LED chip 1600A shown in FIG. 18 may be used instead of the LED chip 1600. FIG. 18 shows configuration and a connection relationship of the flip chip-type LED chip 1600A.

The LED chip 1600A is different from the LED chip 1600 in that the LED chip 1600A is connected to each of the anode pattern 310 and the cathode pattern 320 without a bonding wire. More specifically, the pad 1730 acting as an anode electrode is formed between the semiconductor layer 1720 and the anode pattern 310, and the pad 1740 acting as a cathode electrode is formed between the semiconductor layer 1720 and the cathode pattern 320. This flip chip-type LED chip 1600A may achieve a small mounting area resulting from the non-use of a bonding wire and high light emission efficiency resulting from prevention of light blocking by the electrode, compared to the LED chip 1600.

(Variation 5)

Figure 19:
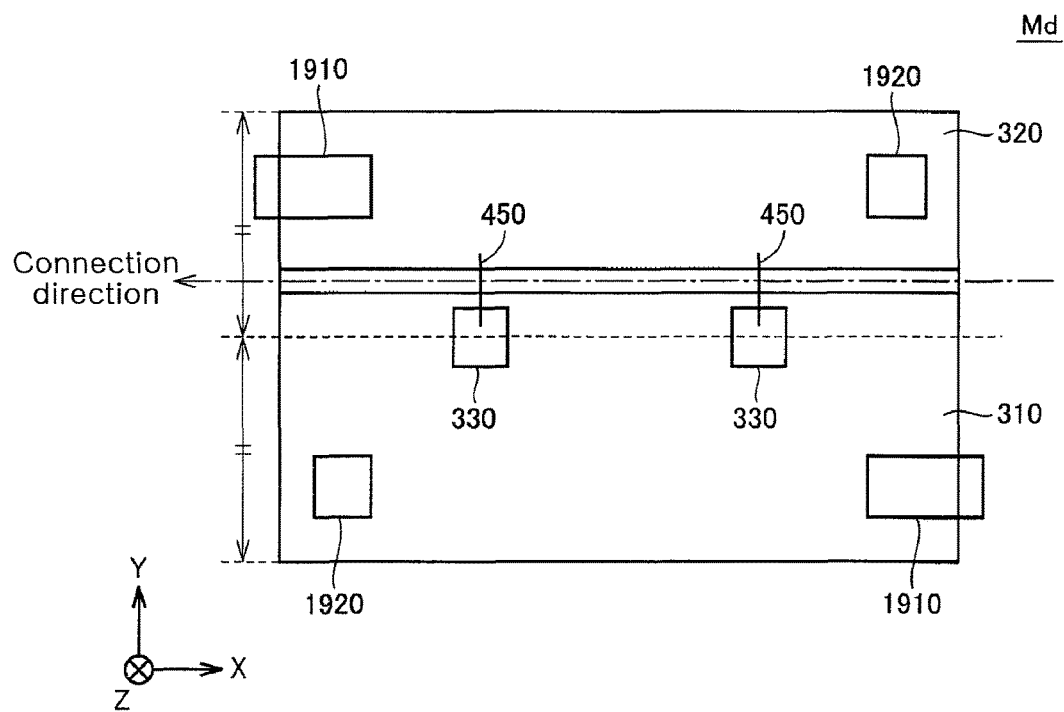
FIG. 19 is a diagram showing configuration of an LED module Md according to variation 5.

FIG. 19 shows configuration of an LED module Md according to variation 5. The LED module Md is different from the LED module M described in FIG. 3 in that the LED module Md has a male connection part 1910 and a female connection part 1920, instead of the connecting part 350.

The LED module Md has the male connection part 1910 and the female connection part 1920 formed in alternating manner at the four corners. That is, the male connection part 1910 and the female connection part 1920 are placed in point symmetry with respect to the center of the LED module Md.

Figure 20:
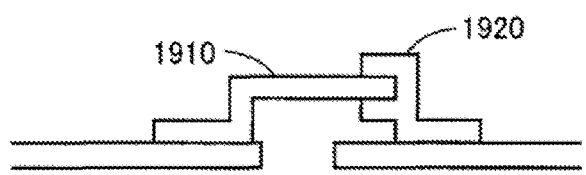
FIG. 20 is a diagram showing a connection relationship of a male connection part 1910 and a female connection part 1920.

FIG. 20 shows a connection relationship of the male connection part 1910 and the female connection part 1920. As shown in FIG. 20, the male connection part 1910 has a convex part, and the female connection part 1920 has a concave part. The convex part and the concave part are configured for insert fitting. The male connection part 1910 and the female connection part 1920 are formed by a conductive member.

By the above configuration, the LED module Md on one side and the LED module Md on other side are electrically connected by insert fitting of the male connection part 1910 and the female connection part 1920. Additionally, the male connection part 1910 and the female connection part 1920 are placed in point symmetry with respect to the center of the LED module Md. By this reason, the LED module Md on the other side may be rotated 180° about the normal line that passes through a geometric center of the exterior shape of the substrate 410 on the XY plane with respect to the LED module Md on one side, and connected to the LED module Md on one side.

(Variation 6)

In the above example, the LED module M includes the multiple LED chips 330 arranged in a line in the connection direction (X direction). However, the multiple LED chips 330 placed on the substrate 410 do not need to be arranged in a line.

Figure 21:
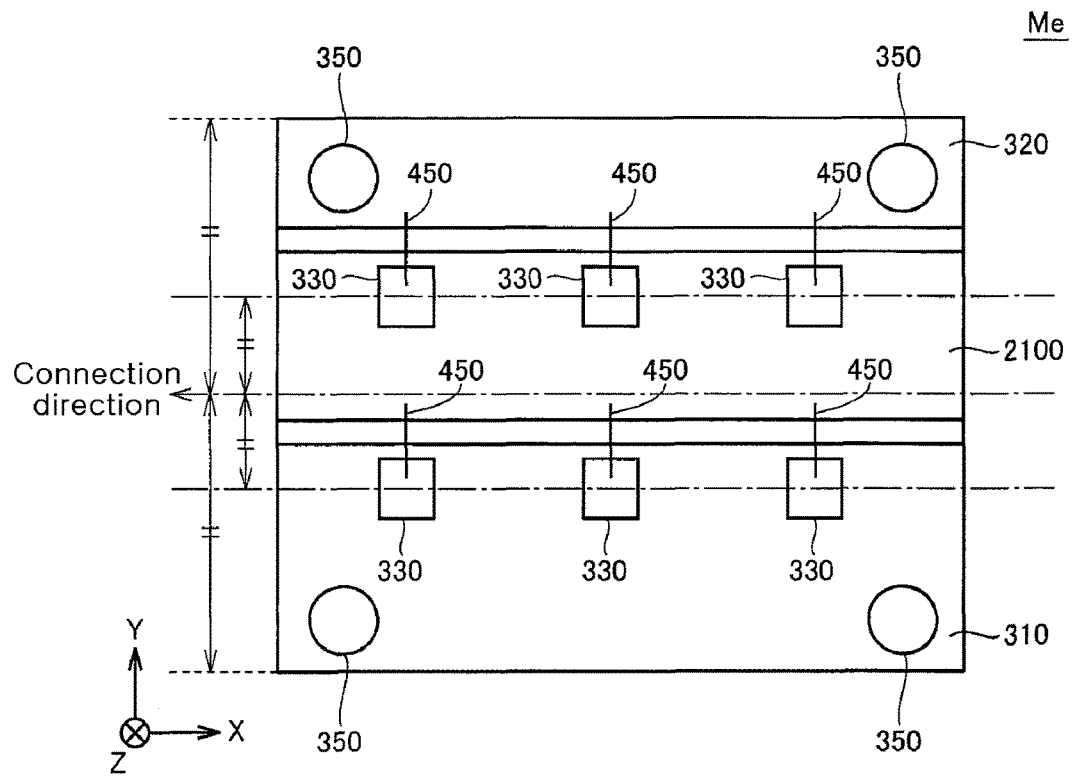
FIG. 21 is a diagram showing configuration of an LED module Me according to variation 6.
Figure 22:
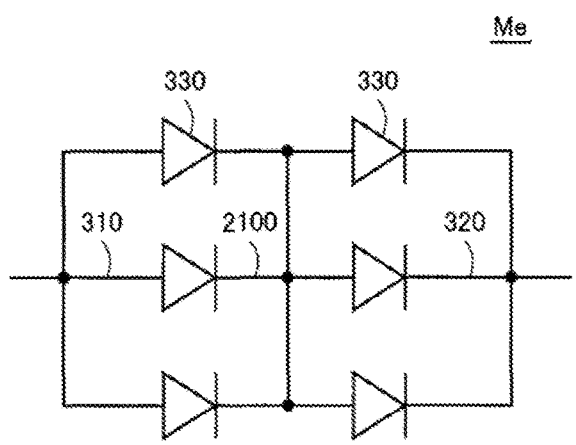
FIG. 22 is a diagram showing an equivalent circuit of the LED module Me shown in FIG. 21.

FIG. 21 shows configuration of an LED Me according to variation 6. FIG. 22 shows an equivalent circuit of the LED module Me shown in FIG. 21. In addition to the anode pattern 310 and the cathode pattern 320, the LED module Me has a central pattern 2100 interposed between the patterns.

The LED module Me has six LED chips 330. More specifically, the LED module Me has three LED chips 330 (hereinafter referred to as ⌈a front array of LED chips 330⌋) placed on the anode pattern 310 along the connection direction (X direction) and three LED chips 330 (hereinafter referred to as ⌈a rear array of LED chips 330⌋) placed on the central pattern 2100 along X direction. The front array of LED chips 330 and the rear array of LED chips 330 are electrically connected to each other in series.

The LED module Me is configured such that the distance from the center position in a direction (Y direction) perpendicular to X direction to the placement position of the front array of LED chips 330 is equal to the distance from the center position from the placement position of the rear array of LED chips 330. Preferably, six LED chips 330 are placed in line symmetry with respect to a straight line extending to the center in Y direction of the LED module Me. More preferably, six LED chips are placed in point symmetry with respect to the normal line that passes through a geometric center of the exterior shape of the LED module Me. Thus, in an LED assembly composed of the multiple LED modules Me, non-uniformity of light illumination intensity in series connection and parallel connection of the LED module Me on one side and adjacent LED module Me on the other side may be suppressed.

As described above, the multiple LED chips 330 placed on the LED module do not need to be arranged in a line in the connection direction (X direction), and may be arranged in multiple lines.

Furthermore, it should be understood that the disclosed embodiments are illustrative in all aspects and are not limitative. The scope of the present disclosure is defined by the appended claims rather than the foregoing description, and is intended to cover all changes within the meaning and scope equivalent to the appended claims.

DETAILED DESCRIPTION OF MAIN ELEMENTS

1 . . . Inspection apparatus
100, 100A, 100B, 100C . . . Light illuminating apparatus
110 . . . IC driver
120 . . . Power device
130 . . . Object of inspection
140 . . . Camera
150 . . . Detection unit
200 . . . Housing
210 . . . Surface
310 . . . Anode pattern
320 . . . Cathode pattern
330, 330A, 1600, 1600A . . . LED chip
350 . . . Connecting part
410, 1710 . . . Substrate
420, 1720 . . . Semiconductor layer
430 . . . Anode electrode
440 . . . Cathode electrode
450 . . . Bonding wire
500 . . . Connection member
510 . . . Bridge member
520 . . . Screw
550, 550A, 550B, 550C . . . LED assembly
1730, 1740 . . . Pad
1910 . . . Male connection part
1920 . . . Female connection part
M, Ma, Mb, Mc, Md, Me . . . LED module
2100 . . . Central pattern

The invention claimed is:

1. A light emitting device, comprising:
a substrate having an anode pattern and a cathode pattern; and
at least one light emitting element connected to the anode pattern and the cathode pattern,
wherein the substrate has a connecting part at each of two ends of the anode pattern extending in a connection direction with other light emitting device that is different from the light emitting device to connect the light emitting device to other light emitting device, and a connecting part at each of two ends of the cathode pattern extending in the connection direction to connect the light emitting device to other light emitting device.

2. The light emitting device according to claim 1, wherein the cathode pattern is formed in a direction perpendicular to the connection direction with respect to the anode pattern.

3. The light emitting device according to claim 2, wherein comprises multiple light emitting elements electrically connected to each other in parallel.

4. The light emitting device according to claim 3, wherein the substrate is rectangular,
the connection direction is a lengthwise direction of the substrate, and
each of the multiple light emitting elements is placed at a widthwise direction center of the substrate.

5. The light emitting device according to claim 1, wherein comprises multiple light emitting elements electrically connected to each other in parallel.

6. The light emitting device according to claim 5, wherein the substrate is rectangular,
the connection direction is a lengthwise direction of the substrate, and
each of the multiple light emitting elements is placed at a widthwise direction center of the substrate.

7. The light emitting device according to claim 5, wherein the light emitting element includes a Light Emitting Diode (LED) element.

8. The light emitting device according to claim 7, wherein each of the multiple LED elements is configured such that non-uniformity of forward direction voltage is 0.2V or less.

9. The light emitting device according to claim 7, wherein each of the multiple LED elements is configured such that non-uniformity of forward direction voltage is 0.1V or less.

10. The light emitting device according to claim 7, wherein each of the multiple LED elements is configured such that non-uniformity of forward direction voltage is 0.05V or less.

11. The light emitting device according to claim 7, wherein the LED element includes an anode electrode, and a cathode electrode placed in a vertical direction of the substrate with respect to the anode electrode,
the anode electrode is connected to the anode pattern, and
the cathode electrode is connected to the cathode pattern.

12. The light emitting device according to claim 7, wherein the LED element includes an anode electrode, and a cathode electrode placed in an approximately horizontal direction of the substrate with respect to the anode electrode,
the anode electrode is connected to the anode pattern, and
the cathode electrode is connected to the cathode pattern.

13. The light emitting device according to claim 1, wherein the connecting part includes a screw hole.

14. A light illuminating apparatus comprising multiple light emitting devices defined in claim 1.

15. The light illuminating apparatus according to claim 14, wherein the multiple light emitting devices include a first light emitting device and a second light emitting device adjacent to the first light emitting device, and
the connecting part installed on the cathode pattern of the first light emitting device and the connecting part installed on the anode pattern of the second light emitting device are electrically connected.

16. The light illuminating apparatus according to claim 14, wherein the multiple light emitting devices include a first light emitting device and a second light emitting device adjacent to the first light emitting device,
the connecting part installed on the anode pattern of the first light emitting device and the connecting part installed on the anode pattern of the second light emitting device are electrically connected, and
the connecting part installed on the cathode pattern of the first light emitting device and the connecting part installed on the cathode pattern of the second light emitting device are electrically connected.

17. The light illuminating apparatus according to claim 16, wherein the light emitting element includes an LED element, and
the light illuminating apparatus is configured such that non-uniformity of forward direction voltage of the LED element placed in the first light emitting device and forward direction voltage of the LED element placed in the second light emitting device is 0.2V or less.

18. The light illuminating apparatus according to claim 16, wherein the light emitting element includes an LED element, and
the light illuminating apparatus is configured such that non-uniformity of forward direction voltage of the LED element placed in the first light emitting device and forward direction voltage of the LED element placed in the second light emitting device is 0.1V or less.

19. The light illuminating apparatus according to claim 16, wherein the light emitting element includes an LED element, and
the light illuminating apparatus is configured such that non-uniformity of forward direction voltage of the LED element placed in the first light emitting device and forward direction voltage of the LED element placed in the second light emitting device is 0.05V or less.

20. The light illuminating apparatus according to claim 14, wherein the multiple light emitting devices include a first light emitting device and a second light emitting device adjacent to the first light emitting device,
the second light emitting device is placed in an arrangement direction of the multiple light emitting elements included in the first light emitting device with respect to the first light emitting device, and
an interval between a light emitting element placed in a closest position to the second light emitting device among the multiple light emitting elements included in the first light emitting device and a light emitting element placed in a closest position to the first light emitting device among the multiple light emitting elements included in the second light emitting device is equal to an interval between adjacent light emitting elements among the multiple light emitting elements included in the first light emitting device.

* * * * *